United States Patent [19]

Faass et al.

[11] Patent Number: 5,496,874

[45] Date of Patent: Mar. 5, 1996

[54] MOLDABLE HYDRODISINTEGRATABLE MATERIAL AND PRODUCTS FORMED THEREBY

[75] Inventors: Judith K. Faass, Dawsonville; Lee K. Jameson, Roswell; Bernard Cohen, Berkeley Lake; Lamar H. Gipson, Acworth, all of Ga.

[73] Assignee: Kimberly-Clark Corporation, Neenah, Wis.

[21] Appl. No.: 333,561

[22] Filed: Nov. 2, 1994

[51] Int. Cl.$^6$ .................... C08L 5/00; C08K 5/05; C08K 5/3415; C08G 63/91

[52] U.S. Cl. .................... 524/56; 524/94; 524/167; 524/173; 524/233; 524/386; 524/387; 525/54.24; 525/54.26

[58] Field of Search .................... 524/386, 513, 524/56, 387, 233, 173, 167, 94, 504; 525/54.24, 54.26; 523/522

[56] References Cited

U.S. PATENT DOCUMENTS

| | | | |
|---|---|---|---|
| 3,365,320 | 1/1968 | Minelli | 106/133 |
| 3,890,974 | 6/1975 | Kozak | 128/287 |
| 3,952,347 | 4/1976 | Comerford et al. | 5/335 |
| 4,028,290 | 6/1977 | Reid | 260/17.4 |
| 4,186,233 | 1/1980 | Krajewski et al. | 428/213 |
| 4,200,558 | 4/1980 | Holst et al. | 260/17 A |
| 4,410,571 | 10/1983 | Korpman | 427/385.5 |
| 4,454,055 | 6/1984 | Richman et al. | 252/194 |
| 4,518,721 | 5/1985 | Dhabhar et al. | 523/120 |
| 4,655,840 | 4/1987 | Wittwer et al. | 106/126 |
| 4,861,539 | 8/1989 | Allen et al. | 264/204 |
| 4,913,517 | 4/1990 | Arroyo et al. | 350/96.23 |
| 5,013,769 | 5/1991 | Murray et al. | 523/111 |
| 5,056,960 | 10/1991 | Marienfeld | 405/270 |
| 5,225,489 | 7/1993 | Prevorsek et al. | 525/151 |
| 5,248,720 | 9/1993 | Deguchi et al. | 524/444 |
| 5,317,037 | 5/1994 | Golden et al. | 523/128 |

FOREIGN PATENT DOCUMENTS

| | | |
|---|---|---|
| 2005764 | 6/1990 | Canada. |
| 0164197 | 12/1985 | European Pat. Off.. |
| 0585906A2 | 3/1994 | European Pat. Off.. |
| 63-304082 | 12/1988 | Japan. |
| 05086344 | 4/1993 | Japan. |
| 06057059 | 3/1994 | Japan. |
| 2048078 | 12/1980 | United Kingdom. |
| 2246373 | 1/1992 | United Kingdom. |

OTHER PUBLICATIONS

*Absorbent Polymer Technology*, Lisa Brannon–Peppas and Ronald S. Harland (eds.), Elsevier, pp. 3–22, Sep., 1990.
B F Goodrich Specialty Polymers & Chemicals Division, *Hystretch® Elastomer Emulsions*, Doc. No. MSDS90.534, Nov. 2, 1990.

*Eastman AQ® Polymers Properties and Applications*, Eastman Chemicals Publication No. GN–389B, pp. 2–27, May, 1990.
Hoechst Celanese Corporation, *Material Safety Data Sheet*, MSDS No. 1101750318, pp. 1–3, Feb. 7, 1992.
"Preparation and Use of Composites Swellable by Water," *Chemcial Abstracts*, vol. 114, No. 12, Abst. No. 114:10386m, Mar. 24, 1991.
"The Structure and Properties of Thixotropic Gels," *Chemical Abstracts*, vol. 30, No. 19, Oct. 10, 1936.
*Die Struktur und die Eigenschaften der thixotropen Gele*, Von B. S. Kandelaky, Kolloid Zeitschrift, V. 74, pp. 200–205, Feb., 1936.
*Principles of Colloid and Surface Chemistry*, Paul C. Hiemenz, 2nd ed., Marcel Dekker, Inc., pp. 782–783, Dec., 1985.
*Kirk–Othmer Encyclopedia of Chemical Technology*, 3rd ed., vol. 5, pp. 118–163, John Wiley & Sons, N.Y.–Chester–Brisbane & Toronto, Mar., 1979.
*Kirk–Othmer Encyclopedia of Chemical Technology*, 3rd ed., vol. 21, pp. 492–505, John Wiley & Sons, N.Y.–Chester–Brisbane & Toronto, Mar., 1983.
*The Condensed Chemical Dictionary*, 10th ed., Gessner G. Hawley, Van Nostrand Reinhold Co., N.Y., p. 838, est. Jul.–Aug., 1981.
*The Condensed Chemical Dictionary*, 10th ed., Gessner G. Hawley, Van Nostrand Reinhold Co., N.Y., p. 14, est. Jul., 1981.
*The Condensed Chemical Dictionary*, 11th ed., Gessner G. Hawley, Van Nostrand Reinhold Co., N.Y., pp. 567–568, 1987.
*Polymer Yearbook 3*, Richard A. Pethrick, Harwood Academic Publishers, Chur–London–Paris–New York, p. 65, Sep., 1986.

*Primary Examiner*—Peter A. Szekely
*Attorney, Agent, or Firm*—Joseph P. Harps

[57] ABSTRACT

Disclosed is a hydrodisintegratable material which, when injection molded into an object, acquires and maintains the desired shape without becoming brittle. Additionally, in the presence of water, the molded object has the ability to rapidly disintegrate and disperse when subjected to standardized agitation testing. The moldable material typically includes: (1) from about 7.5 to about 85 weight percent of at least one water dispersible polymer; (2) from about 7.5 to about 85 weight percent of at least one xerogellant; and (3) at least one volatile material, where the weight percentage of all volatile materials present in the material is within a range which is defined, at its lower end, by the weight percentage of all volatile materials which assures that the material will not become brittle upon being molded and is defined, at its upper end, by the highest weight percentage of all volatile materials which results in the material satisfactorily conforming to the desired physical configuration upon being molded. A process for forming such an object is disclosed.

15 Claims, No Drawings

MOLDABLE HYDRODISINTEGRATABLE MATERIAL AND PRODUCTS FORMED THEREBY

FIELD OF THE INVENTION

The field of the present invention is that of improved waste disposal and, in particular, that of disposable materials which have the ability to environmentally degrade.

BACKGROUND OF THE INVENTION

As was stated in prior U.S. patent application Ser. No. 07/997,797 filed on Dec. 29, 1992, in the names of Bernard Cohen, Lee Jameson and Robert Isaac, for many years the problem of waste disposal has plagued the industries which provide disposable diapers, incontinent garments and feminine care products. While much headway has been made in addressing this problem, one of the weak links has been the inability to create an economical plastic material which will degrade when exposed to natural environmental forces. In particular, those of skill in the art have long sought materials which have the ability to readily dissolve, disperse or disintegrate in water. See, for example, U.K. patent disclosure 2,246,373, U.S. Pat. No. 4,186,233 and European Patent Application Number 0 585 906 A2. Without such a material the ability of the user to dispose of a product by flushing it down the toilet is controlled by the physical geometry of the product and the material handling capabilities of the sewage system and plants which will handle the product. Naturally, these constrictions greatly reduce, if not eliminate, the types of products which can be disposed of via toilet flushing. Furthermore, the ability of products such as disposable diapers, incontinent garments and feminine care products, to disintegrate in a landfill has been quite limited. This is because, historically, a large portion of the components of these products, which may well be biodegradable or photodegradable, are encapsulated in a plastic material which only degrades over a long period of time, if at all. Accordingly, if the plastic at least disintegrated in the presence of water, the internal components could degrade as a result of the rupture of the plastic encapsulation and their subsequent exposure to the forces of natural degradation.

The prior U.S. patent application, Ser. No. 07/997,797, discloses such a material and products formed thereby. The terminology used to describe such a material in that application was "hydrodisintegratable". For purposes of consistency, that terminology will also be adopted for use in the present application. The entirety of U.S. patent application Ser. No. 07/997,797 is hereby incorporated by reference.

One of the areas of interest for applications of such a material is, as was stated above, in feminine care items such as, for example, tampons. In some instances, women attempt to discard the rigid or semi-rigid jacket (typically called the applicator) that holds the tampon by flushing it down a toilet after the tampon has been inserted. Because tampon applicators typically are manufactured from a rigid or semi-rigid plastic material which, at best, only slowly degrades in the environment, this method of disposal has created at least two problems, both of which have plagued society for several years. First, such a method of disposal can lead to clogging of toilets or drain pipes. For this reason, many women, after having experienced a sewage line clogging, have refrained from this method of disposal. The second problem results from the resistance of the applicator to the degrading forces of nature whether they be physical or biological. Municipal waste treatment plants typically do nothing to degrade or otherwise alter the applicator. Accordingly, applicators are released into the environment by these plants in a generally nondegraded state. That is, they are readily recognizable as tampon applicators. Such released applicators show up on the banks of rivers and streams and even are deposited by ocean currents and tides. Of course, those applicators that do find their way to a landfill do not readily degrade in that environment either. Naturally, this result is quite unacceptable from both environmental and aesthetic standpoints.

In conducting additional work with the material disclosed in U.S. patent application Ser. No. 07/997,797, it was discovered that the material generally disclosed therein, while quite satisfactory for use in, for example, film formation, exhibited distinct shortcomings when attempts were made to injection mold the material into shaped products. Typically, the material either: (1) assumed a physical, that is geometrical, configuration which did not satisfactorily conform to that desired by, for example, curling or otherwise physically deforming; or (2) became quite brittle and thus was too fragile to form a satisfactory commercial product.

Accordingly, those of skill in the art developed the view that this material was not satisfactory for use in the formation of injection molded objects. Because of the desirable hydrodisintegratability characteristic of this material, those of skill in the art sought a solution to the problems associated with injection molding the material. The starting point of this quest was the appreciation that products molded from this material either physically deformed as by, for example, curling or otherwise assuming a physical shape which did not conform to the desired shape or became brittle during molding, but never both.

OBJECTS OF THE INVENTION

Accordingly, it is a general object of the present invention to provide a material which readily disintegrates when in the presence of water and which can be satisfactorily formed into a desired object by molding with the application of heat and pressure.

Another general object of the present invention is to provide a process for forming a material which readily disintegrates when in the presence of water and which can be satisfactorily formed into a desired object by molding with the application of heat and pressure.

Still further object and the broad scope of applicability of the present invention will become apparent to those of skill in the art from the details given hereinafter. However, it should be understood that the detailed description of the presently preferred embodiment of the present invention is given only by way of illustration because various changes and modifications well within the spirit and scope of the invention will become apparent to those of skill in the art in view of the following description.

DEFINITIONS

As used herein, the term "xerogellant" refers to a material which, when in a substantially dry state, has the ability to spontaneously imbibe at least about twenty (20) times its own weight in aqueous fluid, for example, tap water. The xerogellant should have the ability to generally retain its original identity after it has imbibed the fluid. For example, a bead, fiber or film formed from a xerogellant will still be recognizable as such after having imbibed the fluid.

As used herein, the term "water dispersible polymer" refers to a polymeric material which is capable of forming a dispersion in an aqueous fluid, for example, tap water, at ambient temperature.

As used herein, the term "volatility" refers to the tendency of a solid or liquid material to pass into the vapor state at a given temperature. The volatility of a component of a liquid or solid is the vapor pressure of the component divided by its mole fraction in the liquid or solid.

As used herein, the term "volatile material" refers to any material having a volatility at standard temperature and pressure (STP) of at least about 24 millimeters (mm) of vapor pressure at twenty five (25) degrees Celsius and one (1) atmosphere of pressure for the pure, that is neat, material. Specific examples of volatile materials include, without limitation, water and plasticizing agents such as glycerin.

As used herein, the term "plasticizing agent" refers to an organic compound which, when added to a high polymer, may increase the ease of processing the high polymer or increase the toughness and flexibility of the high polymer after processing. A plasticizing agent may be able to accomplish all of these. An exemplary plasticizing agent is glycerin. As used herein, the term "hydrodisintegratable" refers to a material which, when subjected to the "hydrodisintegration test", disintegrates into a particulate form where no individual particle is readily apparent to the unaided eye within a time period of about three (3) hours or less. Particles of this size generally have a maximum largest dimension of less than about one (1) millimeter. As used herein, the term "hydrodisintegration test" refers to a test procedure where a molded object having a size of about three (3) millimeters by about five (5) millimeters by about thirteen (13) millimeters is placed into a 150 milliliter beaker holding 140 milliliters of tap water with a pH of about 7 and which is maintained at room temperature and pressure. The water and object are stirred with a magnetic bar using a Nuvona Stir Plate model SP18425 (Thermolyne Company, Dubuque, Iowa) at a speed setting of 6. The time required for the object to disintegrate to a predetermined particle size is noted. Unless otherwise noted, the hydrodisintegration test time is the time it takes the block of material to disintegrate to a particle size where the largest dimension of the particle is less than about one (1) millimeter.

As used herein the term "brittle" is meant to refer to a material which, when a solid block of the material having a thickness of about 6 millimeters (mm), is tested in accordance with ASTM D 2240-86, using a Shore D durometer, four (4) times for a time dependent equilibrium value. To be "brittle", the mean value of the four test values will be less than 50. Such testing should be conducted at standard temperature and pressure and at a relative humidity within the range of from 30 percent to 60 percent. As used herein, "brittle" materials must also have an ultimate stress (sometimes called breaking stress by those of skill in the art) of less than about 650 pounds per square inch (psi) and a strain at maximum load of less than 60% when measured with an Instron model #1122 Tensile Test Instrument at ambient temperature. This instrument is available from Instron of Canton, Mass. As used herein the term "a material which satisfactorily conforms to the desired physical configuration upon being molded" is meant to refer to a material which, when subjected to the temperatures and pressures of a molding operation, for example and injection molding process, is able to perform the function for which it was intended. It is recognized that few items exactly conform to the physical configuration of the mold. All that is necessary is for the molded product to satisfactorily perform its intended function.

SUMMARY OF THE INVENTION

In response to the foregoing difficulties which were experienced in attempts to mold hydrodisintegratable materials, we have developed a moldable, hydrodisintegratable material which is capable of being molded into a desired physical configuration while not becoming brittle as a result of being so molded. The material includes from about 7.5 to about 85 weight percent of at least one water dispersible polymer; from about 7.5 to about 85 weight percent of at least one xerogellant. Importantly, the amount of all volatile materials present is maintained within a range which assures that the material will not become brittle upon being molded while not exceeding an amount which results in the material failing to satisfactorily conform to the desired physical configurations. In other words, if not enough volatile material is present, the resultant molded product will be brittle. Alternatively, if too much volatile material is present, the resultant molded product will unsatisfactorily deform by, for example curling, upon being molded and will not be able to satisfactorily perform its intended function.

Importantly, the material, when molded by the application of heat and pressure, conforms substantially to the desired molded configuration and is not brittle. Additionally, the thus molded object retains the desired molded configuration while still having the ability to hydrodisintegrate in the presence of an agitated aqueous medium such as tap water. We have discovered that the amount of volatile materials present in the moldable material is critical to the ability of the material to retain the desired molded configuration without acquiring undesirable characteristics such as brittleness. In particular, we have discovered that there exists a weight percent range of volatile material concentration below which the molded material is brittle and above which the molded material will unsatisfactorily deform during or as a result of the molding process.

While this range will vary with the composition of the hydrodisintegratable material, we have discovered that when the water dispersible polymer is a high molecular weight amorphous polyester having one or more ionic substituents attached thereto and the xerogellant is a starch grafted sodium polyacrylate, the weight percentage of all volatile material present in the hydrodisintegratable material must be within the range of from about 7.5 to about 9.5. If the percentage is below this range, the resultant molded product will be brittle and, if the percentage is above this range, the resultant molded product will have unsatisfactorily deformed during or as a result of the molding process. More particularly, the weight percent of all volatile materials present may range from about 8.0 to about 9.0 weight percent. Even more particularly, the weight percent of all volatile materials present may be about 8.5 weight percent.

It is envisioned that the water dispersible polymer may be selected from a wide variety of other materials, such as, for example, one or more materials selected from the group including acrylic polymers, polyoxides, vinyl polymers, cellulose derivatives, starch derivatives, polysaccahrides and proteins.

It is also envisioned that the xerogellant may be selected from a wide variety of materials such as, for example, one or more materials selected from the group including sodium carboxymethyl cellulose, derivatives of sodium carboxymethyl cellulose, poly(acrylic acid) salts, poly(ethylene oxide), acrylonitrile-grafted starch, hydrolyzed polyacrylonitrile, poly(vinyl alcohol-sodium acrylate), poly(isobutylene-co-disodium maleate) and starch grafted polyacrylate.

In some embodiments the volatile materials remaining may be selected from the group including water and plasticizing agents. If the volatile material remaining are as a whole or, at least in part plasticizing agents, the plasticizing agent may be selected from one or more of the group including glycerin, sorbitol, glucidol, sucrose, ethylene glycol, propylene glycol, diethylene glycol, polyethylene glycol, acid amide, dimethyl acetamide, dimethyl sulfoxide, methyl pyrrolidone and tetramethylene sulfone.

The invention also encompasses processes for forming an object by molding through the application of heat and pressure the material disclosed herein and the hydrodisintegratable objects formed thereby. Such objects can be any product which is capable of being formed by molding processes such as injection molding. An exemplary product is a tampon applicator.

Typically the process for molding the hydrodisintegratable composition into a hydrodisintegratable object such as, for example, a tampon applicator, will include the steps of: hydrating at least one xerogellant; liquefying the hydrated xerogellant; adding at least one plasticizing agent and at least one water dispersible polymer to the liquified xerogellant; mixing the plasticizing agent, the water dispersible polymer and the liquified xerogellant to form a blend; and heating the blend to a temperature and for a sufficient time to bring the weight percentage of all volatile materials present in the blend to within the range which is defined, at its lower end, by the weight percentage of all volatile materials which assures that the material will not become brittle upon being molded and is defined, at its upper end, by the highest weight percentage which results in the material satisfactorily conforming to the desired physical configuration upon being molded.

In the embodiment where the water dispersible polymer is a high molecular weight amorphous polyester having one or more ionic substituents attached thereto and the xerogellant is a starch grafted polyacrylate, it has been discovered that the weight percent of all volatile materials present should be from at least about 7.5 weight percent to about 9.5 weight percent. By "high molecular weight" it is meant to mean "number average molecular weight of from about 14000 to about 16000." In some embodiments the weight percent of all volatiles present in the blend is brought to within the range of from about 8.0 weight percent to about 9.0 weight percent. More particularly, in some embodiments, the weight percent of volatiles present in the blend is brought to about 8.5 weight percent.

DETAILED DESCRIPTION OF THE INVENTION

The moldable, hydrodisintegratable material of the present invention is formed by placing a xerogellant, desirably in powdered form, in an appropriately sized container and adding water so that the xerogellant is fully hydrated. While any material meeting the definition of a xerogellant may be utilized, exemplary xerogellants include sodium carboxymethyl cellulose, derivatives of sodium carboxymethyl cellulose, poly(acrylic acid) salts, poly(ethylene oxide), acrylonitrile-grafted starch, hydrolyzed polyacrylonitrile, poly(vinyl alcohol-sodium acrylate) and poly(isobutylene-co-disodium maleate). One desirable xerogellant is a starch grafted sodium polyacrylate which may be obtained from Hoechst Celanese Corporation under the trade designation Sanwet IM5000P. If the initial addition of water to the xerogellant does not result in the consistency of the xerogellant and water mixture being that of a liquid, additional water is added until such is the case. This action is only necessary with some xerogellants.

At this time the water dispersible polymer and processing additives such as plasticizing agents are added to the hydrated, liquid mixture of xerogellant and water. In some embodiments, the water dispersible polymer may be added to the mixture of water and hydrated xerogellant in the form of an aqueous dispersion.

While any water dispersible polymer may be utilized, exemplary water dispersible polymers include polymers chosen from the group including high molecular weight amorphous polyesters having one or more ionic sodiosulfo substituents attached thereto. This type of polymer is available from the Eastman Chemical Co. of Knoxville, Tenn., under the trade designation Eastman AQ. In particular, Eastman AQ 55 and AQ 38. Eastman literature, which describes these materials in more detail, is readily available to those of skill in the art. This literature discloses that these materials have a number average molecular weight of from about 14000 to about 16000. Alternatively, the water dispersible polymer may be selected from the group including one or more acrylic polymers, polyoxides, vinyl polymers, cellulose derivatives, starch derivatives, polysaccahrides and proteins.

While any suitable plasticizing agent may be utilized, exemplary plasticizing agents include glycerin, sorbitol, glucidol, sucrose, ethylene glycol, propylene glycol, diethylene glycol, polyethylene glycol, acid amides, dimethyl acetamide, dimethyl sulfoxide, methyl pyrrolidone and tetramethylene sulfone. One exemplary plasticizing agent is 96% USP grade glycerin which may be obtained from the Dow Chemical Company of Midlands, Mich.

The next step in the process is to heat the mixture of hydrated xerogellant, water dispersible polymer and processing agent(s) to a temperature and for a time sufficient to reduce the weight percent of all volatile materials present in the mixture to within the desired range. That is to within the range bounded, on its lower end by the minimum total amount of plasticizing agent(s) necessary to assure that the resultant molded product or object will not be brittle; and bounded, on its upper end by the maximum amount of total plasticizing agents which allows the resultant molded object or product to conform satisfactorily to the physical dimensions, that is configuration, desired so that the resultant product or object is capable of performing the function desired of it. Those of skill in the art will readily recognize that this range will vary with the composition of the hydrodisintegratable material. However, this range can be readily determined for each such composition without undue effort. In the composition which we have dealt with, to date, the xerogellant was a starch grafted polyacrylate and the water dispersible polymer was a high molecular weight amorphous polyester having one or more ionic substituents attached thereto. In this situation, the amount of all volatile material(s) present should be within the range of about 7.5 weight percent to about 9.5 weight percent of the material to be molded. More particularly, the weight percent of volatile materials present should be within the range of from about 8.0 weight percent to about 9.0 weight percent. In some embodiments, the weight percent of volatile materials present may be about 8.5 weight percent. Our research discovered the criticality of this range to the obtaining of a properly molded, non-brittle product which satisfactorily assumes and retains the physical configuration desired to be imparted to it by the molding process. As was stated earlier, if the total amount of volatile materials present is below this range, the resultant molded product is unsatisfactory in that it is brittle. That is, it will crack or break easily and, therefore, is not satisfactory in most, if not all, uses and applications. If the total amount of volatile materials present is above this range, the resultant molded product will curl or otherwise deform to an unsatisfactory degree after its removal from the mold. That is, it will have assume a geometrical configuration which is not desired.

Stated another way, the water, the xerogellant, water dispersible polymer and the processing aids such as plasticizing agents are blended together in a conventional manner so that the final weight percentage of these components, after reduction of the volatile materials present by heat assisted evaporation is from about 7.5 to about 85 weight percent of the water dispersible polymer; from about 7.5 to about 85 weight percent of the xerogellant; and from about 7.5 to about 9.5 weight percent of volatile materials. More particularly, the final weight percentages of these components of the material may range from about 7.5 to about 85 weight percent of the water dispersible polymer; from about 7.5 to about 85 weight percent of the xerogellant; and from about 8.0 to about 9.0 weight percent of volatile materials. Even more particularly, the final weight percentages of these components may range from about 7.5 to about 85 weight percent of the water dispersible polymer; from about 7.5 to about 85 weight percent of the xerogellant; and about 8.5 weight percent of volatile materials.

Of course, within the broad teachings of the present invention, other ranges of xerogellant(s) and water dispersible polymer(s) are possible. For example, the weight percentage of xerogellant may be within about 15 to about 75 weight percent. More particularly, the weight percentage of xerogellant present may be within about 30 to about 60 weight percent. For example, the weight percentage of water dispersible polymer present may be within about 15 to about 75 weight percent. More particularly, the weight percentage of water dispersible polymer present may be within about 30 to about 60 weight percent.

Once again, it has been found that, in order for the moldable, hydrodisintegratable composition to be able to be satisfactorily molded by application of heat and pressure at a later time, it is critical that the weight percent of all volatile materials present be maintained at least at a level satisfactory to assure that the resultant product is not brittle while not being so great as to result in the product curling or otherwise physically deforming substantially after the molding process. This percentage range can be arrived at by two methods. First, the hydrodisintegratable material can be compounded so that, initially, the weight percentage of all volatiles present is within the desired range, Alternatively, the initial weight percentage of all volatile materials present can be higher than the desired range and the heat applied by the molding process can be utilized to drive off an appropriate amount of volatile materials so that the total amount present is reduced to within the desired range. Alternatively, where the initial weight percentage of all volatile materials present is above the desired range, the volatile materials can be driven off through application of, for example heat, so that the desired range is achieved and then the material can be subjected to a molding process.

In any event, it has been found that if the moldable, hydrodisintegratable composition is insufficiently prepared so that the weight percent of all volatile materials remaining in the composition is too high, subsequent molding of the composition by application of heat and pressure results in a molded object which, as a result of physical deformation such as, in some cases, curling, fails to satisfactorily conform to the physical configuration which was originally imparted to it by the molding process. This is not desirable.

On the other hand, it has been found that, if the moldable, hydrodisintegratable composition is heated to a point where the weight percent of all volatile materials present in the composition is unsatisfactorily low, the resulting product is quite fragile in that it is brittle. This, likewise, is not desirable.

After the weight percent of all volatiles present in the composition has been brought within the required range, the resultant solid can be utilized in standard, conventional injection molding processes with very desirable results. In particular, the thus molded objects, for example, tampon applicators, conform very well to the desired molded physical configurations while still retaining satisfactory structural integrity. That is they are not brittle. Importantly, such molded objects still retain the ability to rapidly disintegrate when subjected to agitation in an aqueous medium.

In some embodiments it may be desirable to employ various additives such as antioxidants, antistatic agents, blowing agents, compatibilizers, flame retardants, heat stabilizers, impact modifiers, lubricants, ultraviolet stabilizers, processing aids, surfactants, dispersants, slip agents, mold release agents, etc., as fabricating agents or as modifiers depending on the specific properties which would be desirable to have in the final product.

The invention will now be described with respect to certain specific embodiments thereof.

EXAMPLE I

A masterbatch of material was prepared using a co-rotating, intermeshing twin screw seven zone extruder manufactured from Werner & Pfleiderer Corporation of Ramsey, N.J. One of the hoppers of the twin screw extruder was filled with the water dispersible polymer which was a pellet form of Eastman AQ38. The other hopper was filled with the xerogellant which was in the form of fines of powdered Hoechst Sanwet IM5000P. The fines are sold by Hoechst under the trade designation IM 5000F. A Neptune proportioning pump model #520-A-N3 manufactured by the Neptune Chemical Pump Co. of Lansdale, Pa. was assembled, in conventional manner, to supply liquid to zone 2 of the extruder. The Neptune pump was powered by a one-half horse power, 60 Hz, 1725 rpm General Electric pump. This arrangement has a maximum delivering capacity of 125 grams per minute. Because this is the rate limiting rate, all other proportions were calculated and based on this feed rate.

One thousand one hundred and five milliliters (1,105 ml.) of 96% glycerin was combined with 1,000 milliliters of water to produce an 11.52 weight percent glycerin solution. The glycerin solution was mixed thoroughly and then pumped into the second zone of the extruder using the Neptune pump.

The feed rates of the two materials in the extruder hoppers were adjusted until rates of 50 grams per minute were obtained for each material. The feed rate setting for the pellets was 29 and the feed rate setting for the powder was 180.

These actions resulted in a calculated composition of 43.71%/43.71%/12.59% (xerogellant/water dispersible polymer/glycerin).

The die was removed from the end of the extruder to allow for easier sample flow from the end of the barrel of the extruder.

The sample was then extruded as a 1.5 inch wide strip. At the time of sample collection, the following extruded conditions were recorded:

| | |
|---|---|
| Zone | 1/ 2/ 3/ 4/ 5/ 6/ 7 |
| Extruder Zone Temperatures (C.): | 57/87/119/122/102/100/110 |
| Screw Rpm: | 100 |
| Torque: | 74–91% |
| Pressure: | 210 psi (no die) |
| Head Temp: | 104 degrees Celsius |

The extruded material was divided into four (4) samples with samples 2, 3 and 4 being heat treated (dried) before molding as noted in Table I in a Blue M Constant Temperature Cabinet manufactured by the General Signal Company of Blue Island, Ill. Sample 1 was maintained at room temperature.

TABLE I

| | Drying Temperatures | |
|---|---|---|
| Sample # | Drying Temp (°C.) | Time (hrs.) |
| 1 | 25 | — |
| 2 | 110 | 4.5 |
| 3 | 145 | 4.5 |
| 4 | 165 | 4.5 |

The injection molding was carried out on an Engel EC88 28 ton, 1.5 shot size injection molding machine, model CG812SCSX. This machine is manufactured by the Engel Company of Guleph, Ontario, Canada. The machine was equipped with a mold designed to form a coaster for holding drink glasses. The mold had a gate size of 0.121 inch wide, 0.062 inch high and 0.056 inch long. The injection molded article which was formed had a generally circular shape having a 92mm diameter with a thickness of 5mm. A mold release material was employed. The mold release agent used was Stoner K206 silicone food grade mold release available from Stoner Chemicals Inc. of Quarryville, Pa. After molding, the system was purged using HDPE6007, available from M. Holland Company of Northbrook, Ill. The HDPE6007 had a melt flow measured in accordance with ASTM D 569 of about eight (8).

Injection molding of the sample #1 material was carried out at the following temperature/zone settings:

| Zone | 1 | 2 | 3 | 4 |
|---|---|---|---|---|
| | 279° F. Nozzle | 271° F. Front Temp. | 262° F. Middle Temp. | 232° F. Rear Temp. |

The injection molding was carried out at a pressure of 1,204 psi. The hold pressure was 600 psi and the cooling time was 20 seconds.

Injection molding of the sample #2 material was carried out at the following temperature/zone settings:

| Zone | 1 | 2 | 3 | 4 |
|---|---|---|---|---|
| | 280° F. Nozzle | 270° F. Front Temp. | 250° F. Middle Temp. | 230° F. Rear Temp. |

The injection molding of sample #2 was carried out at a pressure of 1,250 psi. The hold pressure was 600 psi and the cooling time was 20 seconds.

Injection molding of sample #3 was carried out at the following temperature/zone settings:

| Zone | 1 | 2 | 3 | 4 |
|---|---|---|---|---|
| | 300° F. Nozzle | 310° F. Front Temp. | 290° F. Middle Temp. | 280° F. Rear Temp. |

The injection molding of sample #3 was carried out at a pressure of 1275 psi. The hold pressure was 600 psi and the cooling time was 20 seconds.

A second portion of the sample #3 material was modified by adding 2 weight percent of a black colorant, Catalog #2016019, which is manufactured by Spectrum, Inc of Lawrenceville, Ga. This material was injection molded under the same molding conditions as for the unpigmented sample #3 material.

For the unpigmented sample, the mean of four (4) Shore D Hardness measurements, as measured by ASTM D 2240-86, was 59. The average Ultimate Stress (Breaking Stress) Tensile Strength in pounds per square inch (psi) for the pigmented sample #3 samples was about 710 as measured on an Instron Model 1122 Tensile Strength Tester (Instron Inc., Canton, Mass.). The two individual measurements utilized to obtain the 710 average for the unpigmented material were 719 and 702. The strain at maximum load was about 70%. All of these measurements indicate that sample #3 was not brittle.

Injection molding of sample #4 was carried out at the following temperature/zone settings:

| Zone | 1 | 2 | 3 | 4 |
|---|---|---|---|---|
| | 300° F. Nozzle | 310° F. Front Temp. | 290° F. Middle Temp. | 280° F. Rear Temp. |

The injection molding of sample #4 was carried out at a injection pressure of 1407 psi. The hold pressure was 600 psi and the cooling time was 20 seconds.

For this sample the mean of four (4) Shore D Hardness measurements, as measured by ASTM D 2240-86, was 48. The average Ultimate Stress (Breaking Stress) Tensile Strength in psi for two measurements was 509 as measured on an Instron Model 1122 Tensile Strength Tester. The two individual measurements utilized to obtain the 509 average for sample #4 were 417 and 601. The strain at maximum load was about 37%. All of these measurements indicate that sample #4 was quite brittle.

Upon removal from the mold, samples #1 and #2 showed considerable curl losing their shape to an unsatisfactory extent. They were very flexible. Upon removal from the mold, sample #4 was very brittle, breaking on very modest pressure. Upon removal from the mold, sample #3 did not curl or otherwise deform to any significant extent. Sample #4 also was not brittle. That is, it held its shape and did not break when flexed.

The weight percent of total volatiles present in dried samples 2, 3 and 4 and in undried sample 1 was determined by differential thermal analysis. This data is reported in Table II.

TABLE II

| Sample | Wt % Total Volatile (to ~200° C.) |
|---|---|
| #1 | 18 |
| #2 | 11 |

TABLE II-continued

| Sample | Wt % Total Volatile (to ~200° C.) |
|---|---|
| #3 | 8.5 |
| #4 | 5 |

Each of the four samples was subjected to the hydrodisintegration test to determine their hydrodisintegratability. The results are shown in Table III.

TABLE III

Dissolution Rates of Molded Materials

| Sample # | Drying Temp. °C. | Sample Wt. G | Onset of Dissolution (min) | Total Time for Dissolution (min) |
|---|---|---|---|---|
| 1 | None | 0.2845 | 2 | 186 |
| 1 | None | 0.3132 | 4 | 195 |
| 2 | 110 | 0.3327 | 1 | 183 |
| 2 | 110 | 0.3075 | 1 | 181 |
| 3 | 145 | 0.3481 | 2 | 186 |
| 3 | 145 | 0.3648 | 2 | 176 |
| 3 + pigment | 145 | 0.3409 | 1 | 158 |
| 3 + pigment | 145 | 0.3219 | 1 | 165 |
| 4 | 165 | 0.3350 | 2 | 147 |
| 4 | 165 | 0.3230 | 1 | 133 |
| AQ38# | None | 0.2744 | 7 | 397* |

Neat AQ38 molded sample
*Sample did not dissolve. It swelled and broke into small fragments.

Table III demonstrates that the sample #3 materials are hydrodisintegratable in that they hydrodisintegrate generally within a time period of three (3) hours [180 minutes] or less.

While the invention has been described in detail with respect to specific preferred embodiments thereof, it will be appreciated that those skilled in the art, upon attaining an understanding of the foregoing, may readily conceive of alterations to and variations of the preferred embodiments. Such alterations and variations are believed to fall within the scope and spirit of the invention and the appended claims.

What is claimed is:

1. An injection moldable, hydrodisintegratable material comprising:
   from about 7.5 to about 85 weight percent of at least one water dispersible high molecular weight amorphous polyester having one or more ionic sodiosulfo substituents attached thereto;
   from about 7.5 to about 85 weight percent of at least one starch grafted sodium polyacrylate; and
   from about 7.5 to about 9.5 weight percent of at least one volatile material.

2. An injection moldable, hydrodisintegratable material comprising:
   from about 7.5 to about 85 weight percent of at least one water dispersible, high molecular weight amorphous polyester having one or more ionic sodiosulfo substituents attached thereto;
   from about 7.5 to about 85 weight percent of at least one starch grafted sodium polyacrylate; and
   from about 8 to about 9 weight percent of at least one volatile material.

3. The injection moldable, hydrodisintegratable material of claim 1, comprising:
   from about 7.5 to about 85 weight percent of at least one water dispersible high molecular weight amorphous polyester having one or more ionic sodiosulfo substituents attached thereto;
   from about 7.5 to about 85 weight percent of at least one starch grafted sodium polyacrylate; and
   about 8.5 weight percent of at least one volatile material.

4. The injection moldable, hydrodisintegratable material of claim 1, wherein the volatile material is selected from a group consisting of water and plasticizing agents.

5. The injection moldable, hydrodisintegratable material of claim 4, wherein the plasticizing agent is selected from the group consisting of glycerin, sorbitol, glucidol, sucrose, ethylene glycol, propylene glycol, diethylene glycol, polyethylene glycol, acid amide, dimethyl acetamide, dimethyl sulfoxide, methyl pyrrolidone and tetramethylene sulfone.

6. An injection molded, hydrodisintegratable object formed from the material of claim 1.

7. An injection molded, hydrodisintegratable object formed from the material of claim 2.

8. An injection molded, hydrodisintegratable object formed from the material of claim 3.

9. An injection moldable, hydrodisintegratable material comprising:
   from about 7.5 to about 85 weight percent of at least one water dispersible high molecular weight amorphous polyester having one or more ionic sodiosulfo substituents attached thereto;
   from about 7.5 to about 85 weight percent of at least one starch grafted sodium polyacrylate; and
   at least one volatile material, where the weight percentage of all volatile materials present in the material is within a range which:
   is defined, at its lower end, by the weight percentage of all volatile materials which assures that the material will not become brittle upon being molded; and
   is defined, at its upper end, by the highest weight percentage which results in the material satisfactorily conforming to the desired physical configuration upon being molded.

10. The injection moldable, hydrodisintegratable material of claim 9, wherein the volatile material is selected from the group consisting of water and plasticizing agents.

11. The injection moldable, hydrodisintegratable material of claim 10, wherein the plasticizing agent is selected from the group consisting of glycerin, sorbitol, glucidol, sucrose, ethylene glycol, propylene glycol, diethylene glycol, polyethylene glycol, acid amide, dimethyl acetamide, dimethyl sulfoxide, methyl pyrrolidone and tetramethylene sulfone.

12. The injection molded, hydrodisintegratable material of claim 9, wherein when the material is formed into a 3 millimeter by 5 millimeter by 13 millimeter block and subjected to agitation in an aqueous medium, the block disintegrates to particles of a size less than 1 millimeter by 1 millimeter by 1 millimeter in about 3 hours or less.

13. An injection molded, hydrodisintegratable object formed from the material of claim 12.

14. The injection molded, hydrodisintegratable object of claim 13, wherein the object is formed from material which, when formed into a 3 millimeter by 5 millimeter by 13 millimeter block and subjected to agitation in an aqueous medium, the block disintegrates to particles of a size less than 1 millimeter by 1 millimeter by 1 millimeter in about 3 hours or less.

15. The injection moldable, hydrodisintegratable material of claim 1, wherein when the material is formed into a 3 millimeter by 5 millimeter block and subjected to agitation in an aqueous medium, the block disintegrates to particles of a size less than 1 millimeter by 1 millimeter by 1 millimeter in about 3 hours or less.

* * * * *